United States Patent
Makino et al.

(10) Patent No.: US 11,457,795 B2
(45) Date of Patent: Oct. 4, 2022

(54) PROCESSOR FOR ELECTRONIC ENDOSCOPE AND ELECTRONIC ENDOSCOPE SYSTEM

(71) Applicant: HOYA CORPORATION, Tokyo (JP)

(72) Inventors: Takao Makino, Tokyo (JP); Jurgen Glatz, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 322 days.

(21) Appl. No.: 16/642,601

(22) PCT Filed: Nov. 2, 2018

(86) PCT No.: PCT/JP2018/040855
§ 371 (c)(1),
(2) Date: Feb. 27, 2020

(87) PCT Pub. No.: WO2019/088259
PCT Pub. Date: May 9, 2019

(65) Prior Publication Data
US 2020/0345205 A1 Nov. 5, 2020

(30) Foreign Application Priority Data
Nov. 6, 2017 (JP) .............................. JP2017-214016

(51) Int. Cl.
*G06T 5/00* (2006.01)
*A61B 1/00* (2006.01)
*A61B 1/05* (2006.01)

(52) U.S. Cl.
CPC ...... *A61B 1/00006* (2013.01); *A61B 1/00045* (2013.01); *A61B 1/05* (2013.01);
(Continued)

(58) Field of Classification Search
CPC ... A61B 1/00006; A61B 1/00045; A61B 1/05; A61B 1/000095; A61B 1/045;
(Continued)

(56) References Cited

U.S. PATENT DOCUMENTS

2003/0076412 A1   4/2003  Ozawa
2010/0092055 A1*  4/2010  Matsuda ............... G06T 7/0012
                                                        382/128

FOREIGN PATENT DOCUMENTS

CN    101527047         9/2009
CN    107113405 A  *    8/2017    ......... A61B 1/00009
(Continued)

OTHER PUBLICATIONS

Official Communication received in Chinese Patent Application No. 201880056378X, dated Dec. 16, 2021.
(Continued)

*Primary Examiner* — Matthew C Bella
*Assistant Examiner* — Kathleen M Broughton
(74) *Attorney, Agent, or Firm* — Greenblum & Bernstein, P.L.C.

(57) ABSTRACT

A processor for an electronic endoscope includes: a region detection unit configured to detect an enhancement processing target region to be enhanced from pixel information of a captured image of a living tissue; and an enhancement processing unit configured to perform enhancement processing on the enhancement processing target region detected by the region detection unit. The region detection unit is configured to repeat a candidate extraction process of extracting a focused pixel as a candidate for an enhancement processing target region when a signal level value of the focused pixel is smaller than signal level values of two farthest pixels located on both sides farthest from the focused pixel in any one of a plurality of pixel array
(Continued)

directions in a region surrounded by a frame surrounding a region with the focused pixel as a center while changing a size of the frame.

9 Claims, 5 Drawing Sheets

(52) U.S. Cl.
CPC ...... *G06T 5/00* (2013.01); *G06T 2207/10068* (2013.01); *G06T 2207/30096* (2013.01)

(58) Field of Classification Search
CPC . G06T 5/00; G06T 5/008; G06T 2207/10068; G06T 2207/30096; G06T 2207/20012; G02B 23/24
See application file for complete search history.

(56) References Cited

FOREIGN PATENT DOCUMENTS

| JP | 10-289319 | 10/1998 | |
|---|---|---|---|
| JP | 3869698 | 1/2007 | |
| JP | 2013240701 A * | 12/2013 | ............. A61B 1/041 |
| JP | 2016-063928 | 4/2016 | |
| JP | 6001219 B1 * | 10/2016 | ............... A61B 1/00 |
| WO | 2008/152924 | 12/2008 | |
| WO | WO-2012033200 A1 * | 3/2012 | ............... A61B 1/04 |
| WO | WO-2014119047 A1 * | 8/2014 | ......... A61B 1/00009 |

OTHER PUBLICATIONS

International Search Report issued in International Pat. Appl. No. PCT/JP2018/040855, dated Jan. 22, 2019.

* cited by examiner

PROCESSOR FOR ELECTRONIC ENDOSCOPE AND ELECTRONIC ENDOSCOPE SYSTEM

TECHNICAL FIELD

The present invention relates to a processor for an electronic endoscope and an electronic endoscope system that acquire a captured image of a living tissue and perform enhancement processing on the captured image.

BACKGROUND ART

An electronic endoscope device is used for observation and treatment of a living tissue inside a human body. A process of enhancing surface irregularities, which makes a concave portion visible such that the surface irregularities of the living tissue can be observed from a captured image obtained by imaging the living tissue using the electronic endoscope device, is performed on the captured image, and the resultant is displayed on a display. Since a lesion part of the living tissue has more irregularities on the surface than a healthy part, the display of the captured image with enhanced surface irregularities is useful to find the lesion part.

There is known an electronic endoscope device that can reliably highlight a concave portion on a surface of a living tissue and, as a result, can reliably diagnose even a slight lesion part without oversight (Patent Literature 1).

This electronic endoscope device generates a video color signal based on one frame of color pixel signals read from a solid-state image sensor provided at a distal tip of a scope. The electronic endoscope device includes a comparison means for comparing a signal level value of a color pixel signal corresponding to a specific pixel included in one frame of color pixel signals with signal level values of color pixel signals corresponding to all adjacent surrounding pixels adjacent to the surrounding of the specific pixel in a predetermined pixel array direction; and a color balance change means for changing color balance of a video color signal by changing the signal level value of the color pixel signal corresponding to the specific pixel according to a comparison result obtained by the comparing means.

CITATION LIST

Patent Literature

Patent Literature 1: JP 3869698 B2

SUMMARY OF INVENTION

Technical Problem

The electronic endoscope device extracts a concave portion of surface irregularities of a living tissue with a mucous membrane by comparing the signal level values of the color pixel signals corresponding to all the adjacent surrounding pixels adjacent to the surrounding of the specific pixel in the predetermined pixel array direction and a signal level value of the specific pixel, and further, reduces a signal level value of a specific color component of a pixel of the extracted concave portion to create a pixel in which a color of a portion corresponding to the concave portion has been changed, as an image with the enhanced surface irregularities.

In the electronic endoscope device, when extracting a part of the concave portion, the signal level value of the specific pixel is compared with the signal level values of the color pixel signals corresponding to all the adjacent surrounding pixels adjacent to the surrounding of the specific pixel in the specific pixel array direction, but not all the pixels located in the concave portions become pixels to be changed in many cases. Specifically, the adjacent surrounding pixels used in the comparison means are pixels at positions fixed with respect to the specific pixel, more specifically, are neighboring pixels neighboring the specific pixel in the up-down direction, the left-right direction, the upper right-lower left direction, and the upper left-lower right direction. Thus, there is a case where the range of the concave portion is not limited to one pixel but includes several pixels when the captured image is a close-up image that has been imaged close to a living tissue which is an object. In this case, a pixel neighboring to the pixel in the most concave portion is not set as a pixel for which a signal level value of a color pixel signal is to be changed despite being located in the concave portion in some cases. Further, when the concave portion is present in a wide range including the adjacent surrounding pixels, the pixel of the most concave portion is not set as a pixel for which a signal level value of a color pixel signal is to be changed in some cases. In addition to the case where the captured image is the close-up image, there is a case where a size of a concave portion is large and the concave portion covers a range of several pixels in a captured image. Even in this case, the above-described problem is likely to occur. Further, even if the same living tissue is imaged with electronic scopes having different resolutions of captured images, a pixel that is to be extracted as a concave portion and subjected to change processing differs depending on the resolution.

Therefore, an object of the present invention is to provide a processor for an electronic endoscope and an electronic endoscope system capable of performing enhancement processing of a larger number of concave portions than in the related art when acquiring a captured image of a living tissue and performing the enhancement processing of the captured image by improving concave portion extraction accuracy for various large and small concave portions in the captured image or reliably extracting concave portions in the captured image even if the resolution of the captured image is different.

Solution to Problem

One aspect of the present invention is a processor for an electronic endoscope that acquires a captured image of a living tissue and performs enhancement processing. The processor includes: a region detection unit configured to detect an enhancement processing target region to be enhanced from pixel information of a captured image of a living tissue; and an enhancement processing unit configured to perform enhancement processing on the enhancement processing target region detected by the region detection unit.

The region detection unit is configured to repeat a candidate extraction process of extracting a focused pixel as a candidate for an enhancement processing target region when a signal level value of the focused pixel is smaller than signal level values of two farthest pixels located on both sides farthest from the focused pixel in any one of a plurality of pixel array directions in a region surrounded by a frame surrounding a region with the focused pixel as a center while changing a size of the frame, and to define the enhancement processing target region based on pixels extracted as the candidates by changing the size.

It is preferable that the region detection unit define the focused pixel as the candidate for the enhancement processing target region when a difference between each of the signal level values of the farthest pixels and the signal level value of the focused pixel is larger than a threshold 1, which is 2 or more at least at a discretized signal level in the signal level value.

It is preferable that the threshold 1 be larger as the frame size is larger.

It is preferable that the threshold 1 be set according to a location of an organ in a body cavity that is an object of the captured image.

It is preferable that the region detection unit be configured to determine whether the focused pixel is the candidate for the enhancement processing target region when an absolute value of a difference of each of the signal level values of the farthest pixels with respect to the focused pixel is smaller than a threshold 2.

It is preferable that the region detection unit define a pixel, which has been extracted as the candidate for the enhancement processing target region in a pixel array direction more times than a threshold 3 among four pixel array directions of an up-down direction, a left-right direction, an upper left-lower right direction, and an upper right-lower left direction in the frame having the same size in the candidate extraction process, as the enhancement processing target region among pixels extracted as the candidates.

It is preferable that the frame be a frame of $(2 \cdot i + 1) \times (2 \cdot i + 1)$ pixels, where i is a natural number from 1 to 6.

It is preferable that the enhancement processing be processing of reducing the signal level value of the detected enhancement processing target region.

It is preferable that the signal level value be a signal level value of a luminance signal of the captured image, or a signal level value of an R component among RGB components of the captured image.

Another aspect of the present invention is an electronic endoscope system that includes: the processor for an electronic endoscope; and an electronic endoscope which is connected to the processor for an electronic endoscope and outputs the captured image of the living tissue.

Advantageous Effects of Invention

According to the processor for an electronic endoscope and the electronic endoscope system described above, it is possible to perform the enhancement processing of a larger number of concave portions than in the related art by improving the concave portion extraction accuracy for various large and small concave portions in the captured image or reliably extracting the concave portions in the captured image even if the resolution of the captured image is different.

DESCRIPTION OF EMBODIMENTS

A processor of an electronic endoscope system according to the present embodiment extracts regions that need to be enhanced in a captured image obtained by imaging a living tissue in the system, for example, regions of concave portions of the living tissue, and performs the enhancement processing on the regions. The regions that need to be enhanced, for example, the regions of the concave portions have various sizes. In addition, the region of the concave portion in the captured image changes depending on the degree of proximity between an object and an endoscope. Thus, in this embodiment, a candidate extraction process of extracting a focused pixel as a candidate for an enhancement processing target region when a signal level value of the focused pixel is smaller than signal level values of two farthest pixels located on both sides farthest from the focused pixel in any one of a plurality of pixel array directions in a region surrounded by a frame surrounding a region with the focused pixel of a captured image as a center at the time of extracting a region in which a concave portion needs to be enhanced from the captured image is repeated while changing a size of the frame, and the enhancement processing target region is defined based on pixels extracted as the candidates by changing the size. Since the candidate region is extracted by changing the size of the frame in this manner, it is possible to improve the concave portion extraction accuracy for various sizes of concave portions in the captured image. In addition, even when the resolution of the captured image is different, the concave portion in the captured image can be reliably extracted. As a result, it is possible to perform the enhancement processing on a larger number of concave portions than in the related art.

Hereinafter, the electronic endoscope system of the present embodiment will be described in detail with reference to the drawings.

Figure 1:
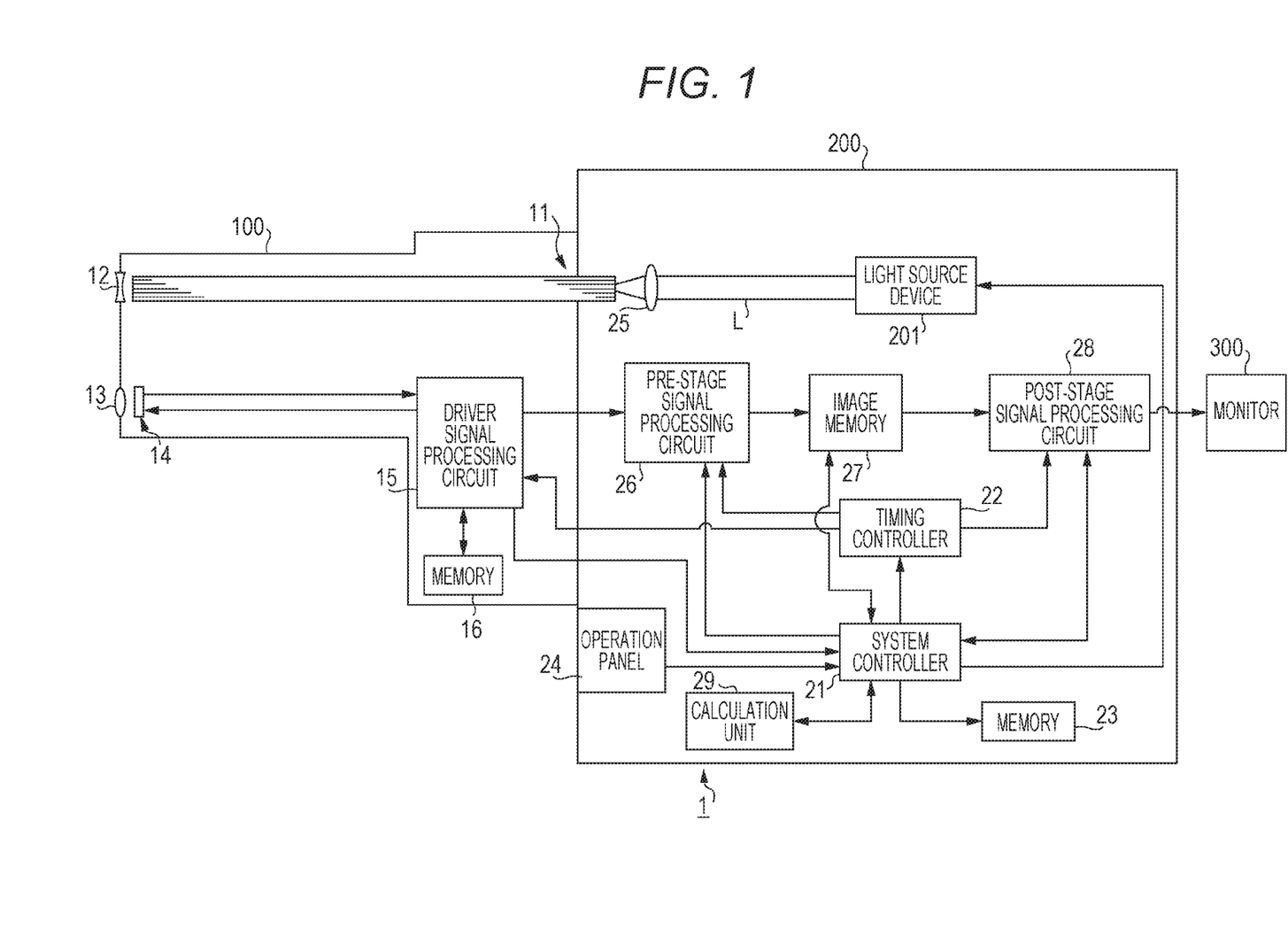
FIG. 1 is a block diagram illustrating an example of a configuration of an electronic endoscope system of the present embodiment.

FIG. 1 is a block diagram illustrating an example of a configuration of an electronic endoscope system 1 of the present embodiment. As illustrated in FIG. 1, the electronic endoscope system 1 is a system specialized for medical use, and includes an electronic scope (endoscope) 100, a processor 200, and a monitor 300.

The processor 200 includes a system controller 21 and a timing controller 22. The system controller 21 executes various programs stored in the memory 23 and integrally controls the entire electronic endoscope system 1. The system controller 21 is connected to an operation panel 24. The system controller 21 changes each of operation of the electronic endoscope system 1 and parameters for each of the operation in accordance with an operator's instruction input to the operation panel 24. The timing controller 22 outputs a clock pulse for adjusting the operation timing of individual units to individual circuits in the electronic endoscope system 1.

The processor 200 includes a light source device 201. The light source device 201 emits illumination light L configured to illuminate an object such as a living tissue in a body cavity. The illumination light L includes white light, pseudo white light, or special light. According to one embodiment, it is preferable that the light source device 201 select one of a mode of constantly emitting white light or pseudo white light as the illumination light L and a mode of alternately emitting white light or pseudo white light and special light as the illumination light L, and emit the white light, the pseudo white light, or the special light based on the selected mode. The white light is light having a flat spectral intensity distribution in the visible light band, and the pseudo white light is light which is a mixture of light of a plurality of wavelength bands and has non-flat spectral intensity distribution. The special light is light in a narrow wavelength band, such as blue and green, in the visible light band. The light in the blue or green wavelength band is used at the time of enhancing and observing a specific portion in a living tissue. The illumination light L emitted from the light source device 201 is focused by the condenser lens 25 onto an incident end face of a Light Carrying Bundle (LCB) 11, which is a bundle of optical fibers, to be incident on the LCB 11.

The illumination light incident on the LCB 11 propagates within the LCB 11. The illumination light L propagating through the LCB 11 is emitted from an exit end surface of the LCB 11 disposed at a distal tip of the electronic scope 100 so as to be directed to the object via a light distribution lens 12. Return light from the object illuminated with the illumination light L from the light distribution lens 12 forms an optical image on a light receiving surface of the solid-state image sensor 14 via an objective lens 13.

The solid-state image sensor 14 is a single-plate color Charge Coupled Device (CCD) image sensor having a Bayer pixel arrangement. The solid-state image sensor 14 accumulates an optical image formed by each of pixels on the light receiving surface, as charges corresponding to the amount of light, and generates and outputs image signals of Red (R), Green (G), and Blue (B). Note that the solid-state image sensor 14 is not limited to a CCD image sensor, and may be replaced with a Complementary Metal Oxide Semiconductor (CMOS) image sensor or other types of imaging devices. The solid-state image sensor 14 may include a complementary color filter.

A driver signal processing circuit 15 is provided in a connection portion where the electronic scope 100 is connected to the processor 200. An image signal of an object is input to the driver signal processing circuit 15 from the solid-state image sensor 14 at a predetermined frame cycle. The frame cycle is 1/30 seconds, for example. The driver signal processing circuit 15 performs predetermined processing on the image signal input from the solid-state image sensor 14 and outputs the processed image signal to a pre-stage signal processing circuit 26 of the processor 200.

The driver signal processing circuit 15 also accesses memory 16 and reads out device-specific information of the electronic scope 100. The device-specific information of the electronic scope 100 recorded in the memory 16 includes, for example, the number of pixels and sensitivity of the solid-state image sensor 14, an operable frame rate, a model number, or the like. The driver signal processing circuit 15 outputs the device-specific information read from the memory 16 to the system controller 21. Examples of this device-specific information may include information unique to an element such as the number of pixels and the resolution of the solid-state image sensor 14, and information regarding an optical system such as an angle of view, a focal length, and a depth of field.

The system controller 21 performs various calculations based on the device-specific information of the electronic scope 100 and generates a control signal. The system controller 21 controls the operation and timing of various circuits in the processor 200 using the generated control signal so as to perform processing suitable for the electronic scope 100 connected to the processor 200.

The timing controller 22 supplies a clock pulse to the driver signal processing circuit 15 in accordance with timing control by the system controller 21. The driver signal processing circuit 15 performs driving control of the solid-state image sensor 14 at a timing synchronized with the frame rate of the video image processed on the processor 200 side in accordance with the clock pulse supplied from the timing controller 22.

The pre-stage signal processing circuit 26 performs predetermined signal processing such as demosaic processing, matrix calculation, and Y/C separation on the image signal input from the driver signal processing circuit 15 in one frame cycle, and outputs the processed signal to the image memory 27.

The image memory 27 buffers the image signal input from the pre-stage signal processing circuit 26, and further buffers an image signal of the enhanced image obtained by performing the enhancement processing on the image signal read from the image memory 27 by the calculation unit 29 again, and outputs the buffered image signal to the post-stage signal processing circuit 28 according to timing control of the timing controller 22.

The post-stage signal processing circuit 28 processes the image signal input from the image memory 27 to generate monitor display screen data, and converts the generated monitor display screen data into a predetermined video format signal. The converted video format signal is output to the monitor 300. With this processing, an image of the object is displayed on a display screen of the monitor 300.

Figure 2:
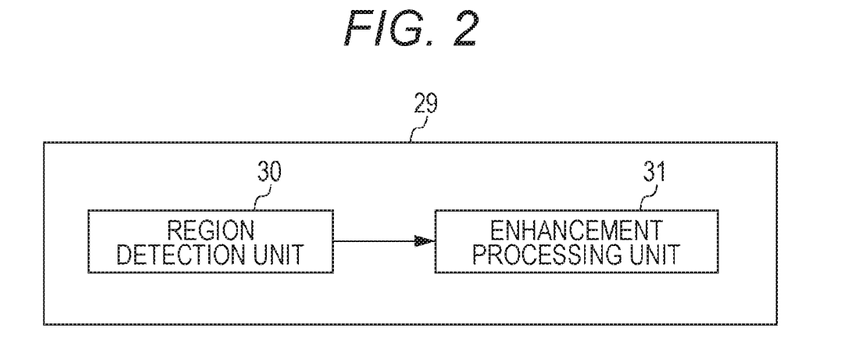
FIG. 2 is a block diagram illustrating an example of a configuration of a calculation unit illustrated in FIG. 1.

The calculation unit 29 is connected to the system controller 21. The calculation unit 29 is a part that extracts a region that needs to be enhanced in a captured image, stored by imaging a living tissue and called from the image memory 27 via the system controller 21, for example, a region of a concave portion of the living tissue, and performs enhancement processing on this region. FIG. 2 is a block diagram illustrating an example of a configuration of the calculation unit 29. The calculation unit 29 includes a region detection unit 30 and an enhancement processing unit 31.

The region detection unit 30 is configured to detect an enhancement processing target region that is to be enhanced from information on pixels of the captured image of the living tissue. As a region detection process, the region detection unit 30 uses a frame surrounding a region centered on a focused pixel to be described below to perform a candidate extraction process of extracting a candidate for an enhancement processing target region while repeatedly changing a size of the frame, and defines an enhancement processing target region based on pixels extracted as candidates. Here, the candidate extraction process is a process of extracting a focused pixel as a candidate for the enhancement processing target region when a signal level value of the focused pixel is smaller than signal level values of two farthest pixels located on both sides farthest from the focused pixel in any one of a plurality of pixel array directions in a region surrounded by a frame surrounding a region with the focused pixel as a center. Therefore, even if it is difficult to extract a candidate pixel in a frame of a certain size, a candidate pixel is extracted in a frame of another size in some cases. Details will be described later.

The enhancement processing unit 31 is configured to perform enhancement processing on the enhancement processing target region detected by the region detection unit 30. Although the enhancement processing is not particularly limited, the enhancement processing includes a process of changing a signal level value of a region corresponding to a concave portion to enhance the concave portion as will be described later.

For example, when a pixel position of a focused pixel of each color component of RGB in an RGB color captured image is expressed as (i,j), the enhancement processing unit 31 uses difference data $\Delta R_{ij}$ between a value $R_{ij}$ of pixel data of the focused pixel and an average value of pixel data of surrounding pixels to calculate enhanced pixel data $r_{ij}$ according to the enhanced pixel data $r_{ij}=R{ij}+k \cdot \Delta R_{ij}$. Here, k is a value set in advance or a value input and set from the operation panel 24. The above k may be a constant value or a value that changes according to a predetermined condition. In addition, k may be different for each color component. Here, the surrounding pixels may be the two farthest pixels that have been compared with the signal level value of the focused pixel when defining the above-described enhancement processing target region, may be eight neighboring pixels surrounding the focused pixel in the up-down direction, the left-right direction, the upper right-lower left, and the upper left-lower right, or may be eight farthest pixels farthest from the focused pixel in the up-down direction, the left-right direction, the upper right-lower left direction, and the upper left-lower right direction in the frame. When the surrounding pixels are the two farthest pixels that have been compared with the signal level value of the focused pixel when defining the enhancement processing target region, $\Delta R_{ij}$ represents a difference between the signal level value $R_{ij}$ of the focused pixel and an average value of the signal level values of the two farthest pixels on the frame. Since $\Delta R_{ij}$ is information corresponding to a recess depth of the concave portion in this manner, the signal level value is greatly changed for a pixel of a concave portion with a deeper recess, so that it is possible to obtain an image in which the region of the concave portion has been enhanced.

Figure 3:
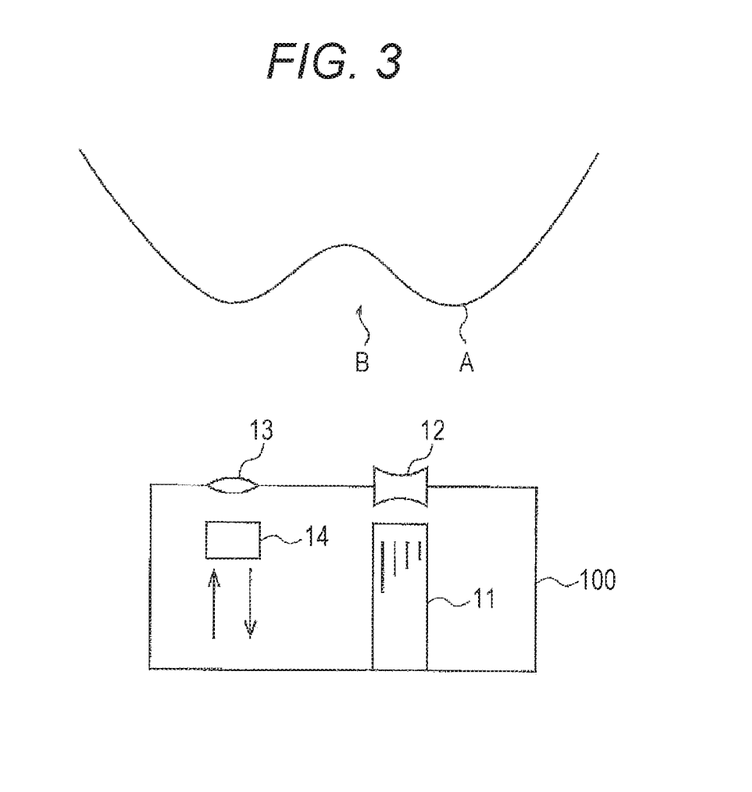
FIG. 3 is a view illustrating an example of imaging of a living tissue by an endoscope illustrated in FIG. 1.

FIG. 3 is a view illustrating an example of imaging of a living tissue A by the electronic scope (endoscope) 100. The living tissue A has a concave portion B that is recessed in the depth direction when viewed from the electronic scope 100. The electronic scope 100 images the living tissue A including the concave portions B.

Figure 4:
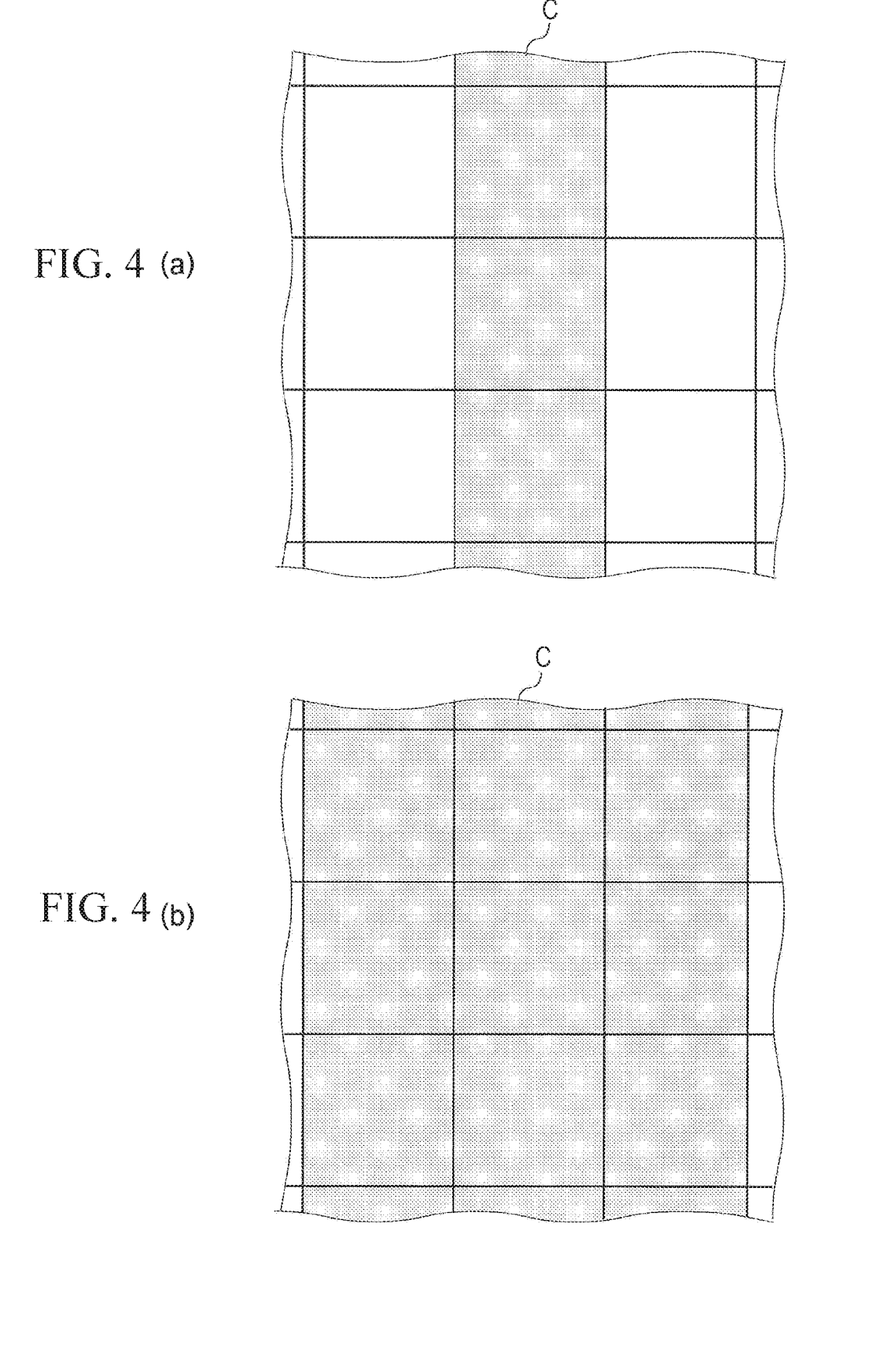
FIGS. 4(a) and 4(b) are views illustrating examples of a captured image which is obtained by the electronic endoscope system and includes a region of a concave portion of an object.

FIGS. 4(*a*) and 4(*b*) are views illustrating examples of a captured image which is obtained by the electronic endoscope system 1 and includes a region C corresponding to the concave portion B. In this case, a size of the region C in the obtained captured image changes depending on a shooting distance of the electronic scope 100 to the living tissue A. In FIGS. 4(*a*) and 4(*b*), the region C indicates a gray region corresponding to the groove-shaped concave portion B extending in one direction. The captured image illustrated in FIG. 4(*b*) has a shorter shooting distance (distance between the object and the solid-state image sensor 14) than the captured image illustrated in FIG. 4(*a*). Thus, the width of the region C may be one pixel in size as illustrated in FIG. 4(*a*), or the width of the region C may exceed a size of one pixel as illustrated in FIG. 4(*b*). In consideration of the region C whose size changes depending on the shooting distance in this manner, the region detection unit 30 has a plurality of frames surrounding a region around a focused pixel with the focused pixel used at the time of performing the region detection process as the center pixel.

Note that the calculation unit 29 may be a software module that is formed as a module when the system controller 21 starts up a program stored in the memory 23, and may be a hardware module configured with a Field-Programmable Gate Array (FPGA).

Figure 5:
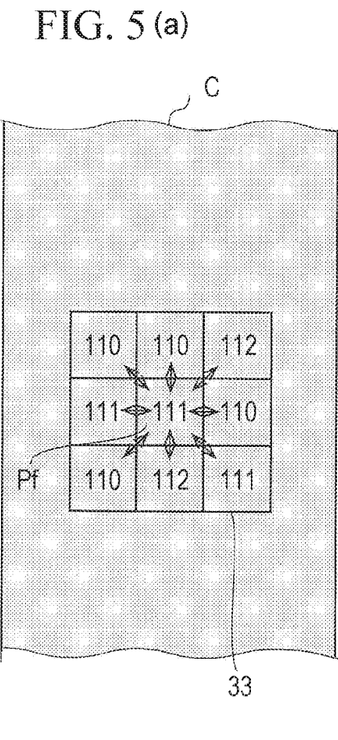
FIGS. 5(a) to 5(c) are views illustrating examples of a process performed by a calculation unit of the present embodiment.

FIGS. 5(*a*) to 5(*c*) are views illustrating examples of processing performed by the region detection unit 30 of the calculation unit 29. FIGS. 5(*a*) to 5(*c*) illustrate a frame 33 of 3×3 pixels, a frame 55 of 5×5 pixels, and a frame 77 of 7×7 pixels as examples. The frames 33, 55, and 77 are arranged such that each pixel at the center of the frame matches the focused pixel in the captured image. Numerical values illustrated in the pixels in FIGS. 5(*b*) and 5(*c*) are examples of signal level values of pixels. The signal level value at the focused pixel is 111.

The region detection unit 30 extracts a focused pixel Pf as a candidate for the enhancement processing target region when a signal level value of the focused pixel Pf is smaller than signal level values of two farthest pixels located on both sides farthest from the focused pixel Pf in any of the up-down direction, the left-right direction, the upper right-lower left direction, and the upper left-lower right direction in a region surrounded by the frame 33 surrounding the region around the focused pixel Pf of the captured image, for example. In general, illumination light L does not reach a concave portion sufficiently at the time of imaging, and return light of the illumination light L does not sufficiently reach a light receiving face of the solid-state image sensor 14, and thus, the concave portion appears as a dark region in the captured image. Thus, it is possible to extract a candidate for the region corresponding to the concave portion by examining whether the signal level value of the focused pixel is smaller than the signal level value of any of the farthest pixels.

When it is difficult to extract the candidate for the region corresponding to the concave portion in the frame 33, the same process as the above process is performed using the frame 55 instead of the frame 33. In this case, in the example illustrated in FIG. 5(*b*), two farthest pixels farthest from the focused pixel Pf and located on both sides in the up-down direction are the pixels Pu and Pd. When it is also difficult to extract a candidate for the region corresponding to the concave portion in the frame 55, the same process as the above process is further performed using the frame 77 instead of the frame 55. In the example illustrated in FIG. 5(*b*), it is difficult to extract the candidate for the region corresponding to the concave portion. In the example illustrated in FIG. 5(*c*), it is possible to extract a candidate for the region corresponding to the concave portion in the left-right direction, the upper right-lower left direction, and the upper left-lower right direction.

Note that there is a case where no farthest pixel exists in a frame when a focused pixel is located at one of upper, lower, left, and right ends f a captured image or is located in the vicinity thereof. In this case, the process of extracting the candidate in any of the up-down direction, the left-right direction, the upper right-lower left direction, and the upper left-lower right direction is not performed.

The region detection unit 30 defines the enhancement processing target region based on the pixels extracted as the candidates by changing the size of the frame. For example, a pixel with the number of times of being set as candidates in the pixel array directions of the left-right direction, the upper right-lower left direction, and the upper left-lower right direction for the same pixel larger than a preset threshold count is defined as the enhancement processing target region. That is, the region detection unit 30 defines a pixel, which has been extracted as the candidate for the enhancement processing target region in the pixel array direction more times than the threshold count (threshold 3) among the four pixel array directions of the up-down direction, the left-right direction, the upper left-lower right direction, and the upper right-lower left direction in the frame of the same size in the candidate extraction process, as the enhancement processing target region. When the threshold count is zero, all the pixels extracted as candidates are set as the enhancement processing target regions. If the threshold count is one or more, a pixel that has been extracted as a candidate more times than the threshold count is set as the enhancement processing target region among pixels that have been extracted as candidates. In the examples using the frames 33, 55 and 77 illustrated in FIGS. 5(a) to 5(c), the focused pixel Pf is extracted as the candidate three times since the signal level value of i11 of the focused pixel Pf is smaller than signal level values (signal level values of 115 and 125, signal level values of 120 and 113, and signal level values of 117 and 118) of two farthest pixels located on both sides farthest from the focused pixel Pf (the signal level value of 111) in the left-right direction, the upper right-lower left direction, and the upper left-lower right direction as illustrated in FIG. 5(c). Thus, the focused pixel Pf is set as the enhancement processing target region in the example illustrated in FIG. 5(c).

Figure 6:
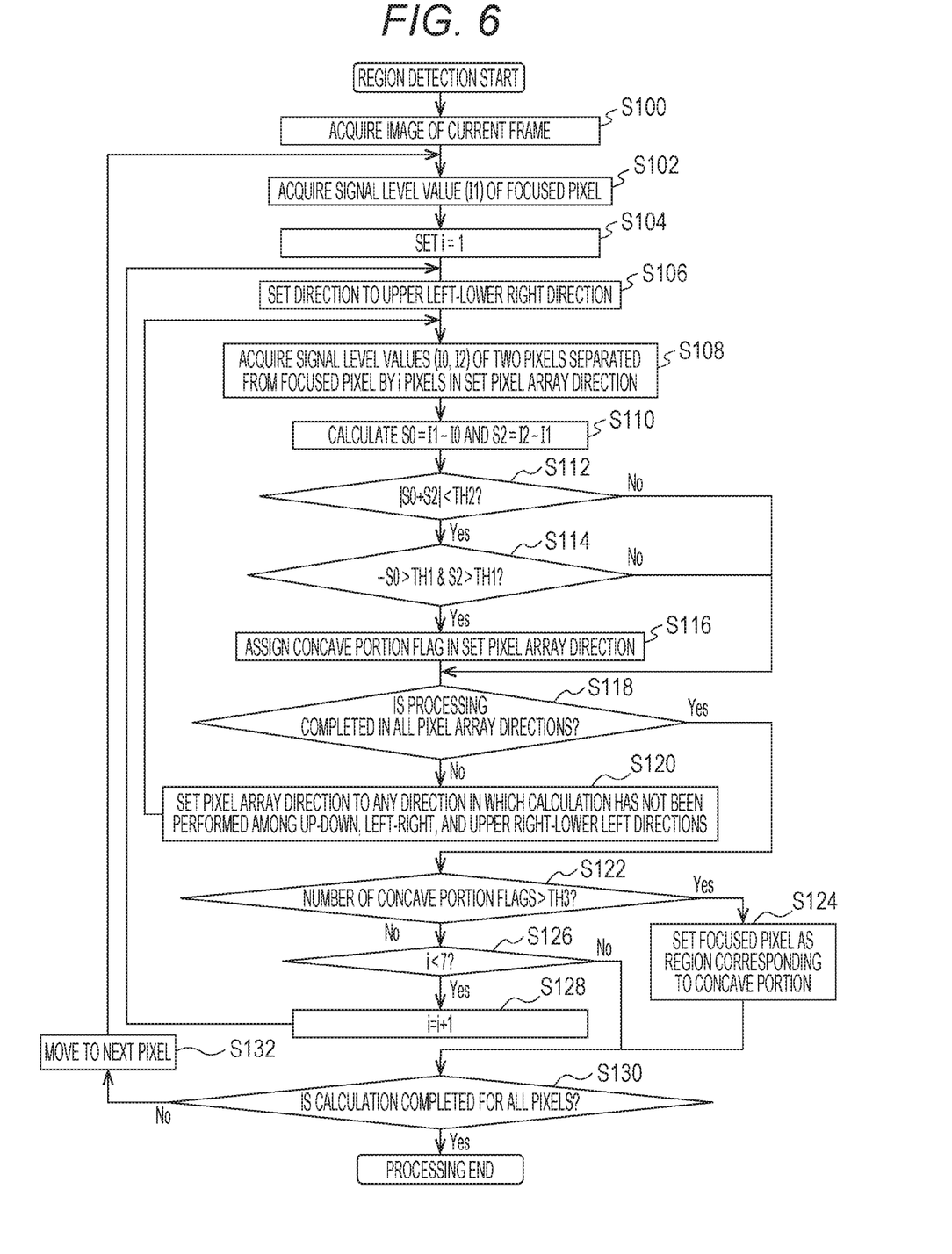
FIG. 6 is a flowchart illustrating an example of a flow of a region detection process of one embodiment performed by the electronic endoscope system.

FIG. 6 is a flowchart illustrating an example of a flow of the region detection process according to the embodiment, which is performed by the region detection unit 30.

The region detection unit 30 calls a captured image of a current frame captured by the electronic scope 100 and stored in the image memory 27 via the system controller 21 to acquire the captured image (Step S100).

Next, the region detection unit 30 defines a focused pixel, and acquires a signal level value of the pixel (Step S102). It is assumed that the signal level value of the focused pixel is 11.

Next, the region detection unit 30 sets a variable i to 1 and selects a frame of (2·i+1)×(2·i+1) pixels (Step S104).

The region detection unit 30 arranges the selected frame on the captured image such that a center pixel of the selected frame matches the focused pixel, and sets a pixel array direction for the focused pixel to the upper left-lower right direction (Step S106). The region detection unit 30 acquires signal level values of two farthest pixels located on both sides in the frame in the set pixel array direction from the focused pixel (Step S108). At this time, the signal level values of the two farthest pixels are defined as I0 and I2.

The region detection unit 30 calculates I1−I0 and I2−I1, and sets difference results to S0 and S2, respectively (Step S110).

Next, the region detection unit 30 determines whether a result of calculating an absolute value of S0+S2 is smaller than a predetermined threshold TH2 (Step S112). Here, the absolute value of S0+S2 is an absolute value of a difference between the signal level values of the two farthest pixels, which has a significance that it is determined whether the absolute value of the difference between the signal level values of the two farthest pixels is smaller than the threshold TH2. If the determination is negative (No), the region detection unit 30 determines that the focused pixel is not a candidate for the enhancement processing target region in the set pixel array direction, and causes the processing to proceed to Step S118 which will be described later. On the other hand, if the determination is affirmative (Yes), the region detection unit 30 determines whether −S0 and S2 are larger than a threshold TH1 (Step S114). If the determination is negative (No), the region detection unit 30 determines that the focused pixel is not a candidate for the enhancement processing target region in the defined pixel array direction, and causes the processing to proceed to Step S118 which will be described later. On the other hand, if the determination in Step S114 is affirmative (Yes), the region detection unit 30 determines that the focused pixel is the candidate for the enhancement processing target region (candidate for a region corresponding to a concave portion) the set pixel array direction, and assigns a concave portion flag to a pixel information recording region set for each pixel array direction corresponding to the focused pixel (Step S116).

Next, the region detection unit 30 determines whether Steps S108 to S118 have been executed for all the pixels in the pixel array direction (Step S118). If the determination is negative (No), the region detection unit 30 sets the pixel array direction in which the processing of Steps S108 to S118 is performed to one of the pixel array directions that have not been set (Step S120). In this manner, the processing of Steps S108 to 120 is repeated while changing the pixel array direction until the determination in Step S118 becomes affirmative (Yes). If the determination in Step S118 is affirmative (Yes), the region detection unit 30 determines whether the number of times the concave portion flag has been given in the current focused pixel exceeds a set threshold count TH3 (Step S122). If the determination is affirmative, the region detection unit 30 sets the focused pixel as the enhancement processing target region (the region corresponding to the concave portion) (Step S124). Thereafter, the processing proceeds to Step S130 which will be described later in order to change the focused pixel. The threshold count TH3 may be once, but is preferably twice or more times in order to enhance the extraction accuracy of the region corresponding to the concave portion.

If the determination in Step S122 is negative (No), it is determined whether the set variable i is smaller than 7, that is, whether all the frames of (2·i+1)×(2·i+1) pixels smaller than the frame of 15×15 pixels have been selected (Step S126). If the determination is affirmative (Yes), the region detection unit 30 increases the variable i by 1 (Step S128), that is, increases the frame size, and returns the processing to Step S106. Thus, the region detection unit 30 repeats Steps S106 to S124 while gradually increasing the frame size until the determination in Step S126 is affirmed (Yes).

If the determination in Step S126 is negative (No) or if the focused pixel is set as the enhancement processing target region (the region corresponding to the concave portion) in Step S124, the region detection unit 30 determines whether the calculation of the above processing has been completed with all the pixels of the captured image as the focused pixel (Step S130). If the determination is negative (No), the region detection unit 130 moves the focused pixel to the next pixel and sets the next pixel as a focused pixel (Step S132). If the determination in Step S130 is affirmative (Yes), the region detection unit 130 ends the region detection process. In this manner, the processing of Steps S102 to S132 is repeated until the region detection process is performed for all the pixels of the captured image.

In this manner, the region detection unit 30 is configured to repeat the candidate extraction process of extracting the focused pixel as the candidate for the enhancement processing target region when the signal level value of the focused pixel is smaller than the signal level values of the two farthest pixels in any one of the plurality of pixel array directions in the region surrounded by the frame surrounding the region around the focused pixel in the captured image while changing the frame size, and to define the enhancement processing target region based on the candidate pixels extracted as the candidates by changing the size. Here, the candidate extraction process corresponds to processing of Steps S106 to S120 in the example of the flow illustrated in FIG. 6. Thus, it is possible to improve the concave portion extraction accuracy with respect to various sizes of concave portions in the captured image. In addition, even when the resolution of the captured image (distance on the object corresponding to a length of one side of each pixel) is different, the concave portion in the captured image can be reliably extracted. As a result, it is possible to perform the enhancement processing on a larger number of concave portions than in the related art.

According to the embodiment, it is preferable that the threshold TH2 to be compared with the difference between the signal level values of the farthest pixel and the signal level value of the focused pixel be 2 or more at least in the discretized signal level.

For example, in a 10-bit discretized signal level, the threshold TH2 is preferably 32 to 64. A mucous membrane is present on a surface of the living tissue, and the reflectivity fluctuates due to the mucous membrane. Thus, a signal level value exhibits a change similar to the concave portion even if there is no concave portion. However, when the threshold TH2 is set within the above range, it is possible to distinguish the concave portion of the living tissue from a similar change that is likely to be erroneously recognized as the concave portion.

According to the embodiment, it is preferable that the threshold TH1 be larger as the frame size is larger. As the frame size increases, a distance between the focused pixel and the farthest pixel increases, and a similar change that is likely to be erroneously recognized as the concave portion can be easily extracted in the region detection process. Therefore, it is preferable that the threshold TH1 be larger as the frame size is larger.

It is preferable that the region detection unit 30 be configured to determine whether the focused pixel is the candidate for the enhancement processing target region when the absolute value of the difference between the signal level values of the farthest pixels is smaller than the threshold TH2. In the example illustrated in FIG. 6, when the determination in Step S112 is affirmative, the determination on the candidate for the enhancement processing target region (region of the concave portion) is performed in Step S114. As a result, it is possible to suppress deterioration in reliability of extraction of the candidate even for a captured image in which the reliability of the extraction of the candidate for the region corresponding to the concave portion is likely to be low due to the large change in the signal level value of the captured image.

It is preferable that the thresholds TH1 and TH2 be set in advance. According to the embodiment, it is preferable that the thresholds TH1 and TH2 hold related information associated with e thresholds TH1 and TH2 for each part of an organ in a body cavity. According to the embodiment, it is preferable to configure the processor 200 so as to be instructed with the input of the information from the operation panel 214 on any part of any organ to which the living tissue to be imaged corresponds, and to set the thresholds TH1 and TH2 using the related information from the input and instructed information. In addition, according to the embodiment, it is preferable to measure a distance at which the electronic scope 100 is inserted, automatically determine any part of any organ to which the living tissue to be imaged corresponds based on the measured distance, and to set the thresholds TH1 and TH2 using a determination result and the related information. That is, it is preferable that the thresholds TH1 and TH2 be set according to a location of the organ in the body cavity that is the object of the captured image.

It is preferable for the region detection unit 30 to define, as the enhancement processing target region, a pixel that has been extracted as a candidate for the enhancement processing target region at least twice or more, a pixel to which the concave portion flag has been assigned twice or more in the example illustrated in FIG. 6 among the pixels extracted as candidates for the enhancement processing target region (region of the concave portion) in that it is possible to reliably extract a point-shaped concave portion or a groove-shaped concave portion extending in one direction.

According to the embodiment, it is preferable that the enhancement processing performed on the extracted enhancement processing target region be processing of reducing the signal level value of the extracted enhancement processing target region. Since regions corresponding to a plurality of concave portions having different sizes can be extracted as the enhancement processing target regions using a plurality of frames having different frame sizes in the extraction of the enhancement processing target region, it is possible to reliably obtain the image with the enhanced concave portion by reducing the signal level value of the extracted enhancement processing target region.

According to the embodiment, it is preferable that a signal level value of a pixel used for extraction of the enhancement processing target region be a signal level value of a luminance signal of the captured image or a signal level value of an R component of RGB components when the captured image is a color image. The concave portion is a portion where reflected light of the living tissue hardly enters and is a portion with low luminance, and thus, using the signal level value of the luminance signal is suitable in the case of extracting the region corresponding to the concave portion as the enhancement processing target region. On the other hand, the living tissue absorbs light in a wavelength band of a blue component and a green component, it is difficult to distinguish the region of the concave portion from a region darkened by the light absorption. Thus, it is preferable when the region corresponding to the concave portion of the living tissue is extracted as the enhancement processing target region using the signal level value of the R component.

Although a total of six types of frames from the minimum frame of 3×3 pixels to the frame size of 13×13 pixels have been used as the frame sizes in the flow illustrated in FIG. 6, there is no particular limitation on the frame size and the number of frames to be used. According to the embodiment, it is preferable that an upper limit of the frame size be a size equal to or smaller than 13×13 pixels in order to accurately extract the region of the concave portion. In the electronic endoscope system 1, in many cases, different types (different specifications) of the electronic scopes 100 are used by replacing the electronic scope 100 for the single processor 200. Since the resolution of an image of the solid-state image sensor 14 is often different depending on the type of the electronic scope 100, a size of the region corresponding to the concave portion in the captured image changes as illustrated in FIGS. 4(*a*) and 4(*b*) depending on the type of the electronic scope 100 used for imaging even if the same concave portion of living tissue is imaged. Thus, even in the case of the captured image of the living tissue including the same concave portion, the extraction of the region corresponding to the concave portion becomes unstable (is not extracted in some cases or extracted in other cases). For this reason, the enhancement of the concave portion is also unstable (is not extracted in some cases or extracted in other cases) in an enhanced image, and there is a case where it is difficult to visually recognize the same concave portion. On the other hand, the concave portion in the captured image can be reliably extracted even if the resolution of the captured image is different in the above-described embodiment. As a result, the enhancement processing of the concave portion can be performed more reliably than in the related art.

Therefore, according to the embodiment, it is preferable that the region detection unit 30 set at least one of the number of frames and the frame size to be used in the region detection unit 30 based on information of an image sensor such as the resolution and the total number of pixels of the solid-state image sensor 14, and imaging-specific information including optical information relating to an optical system such as an angle of view, a focal length, and a depth of field. Since a range of a length of the object occupying one pixel of the captured image can be known from the imaging-specific information, the size of the region of the concave portion in the captured image can be estimated to some extent from the range of the length. Therefore, at least one of the number of frames and the frame size can be set based on this estimation. In this case, it is preferable that related information in which the above-described imaging-specific information is associated with the frame size and the number of frames be stored in the memory 23 in advance. When the electronic scope 100 is connected to the processor 200, the electronic scope 100 reads unique information relating to the electronic scope 100 from the memory 16 and outputs the read information to the system controller 21. Therefore, according to the embodiment, it is preferable that the region detection unit 30 automatically set the frame size and the number of frames corresponding to the type of the connected electronic scope 100 using the above related information stored in the memory 23 from the imaging-specific information included in the unique information transmitted from the electronic scope 100.

Although the processor for an electronic endoscope and the electronic endoscope system of the present invention has been described in detail as above, the processor for an electronic endoscope and the electronic endoscope system of the present invention are not limited to the above-described embodiment, and may of course be modified or altered in various ways in a range not deviating from the spirit of the present invention.

REFERENCE SIGNS LIST

1 Electronic endoscope system
11 LCB
12 Light distribution lens
13 Objective lens
14 Solid-state image sensor
15 Driver signal processing circuit
16 Memory
21 System controller
22 Timing controller
24 Operation panel
25 Condenser lens
26 Pre-stage signal processing circuit
27 Image memory
28 Post-stage signal processing circuit
29 Calculation unit
30 Region detection unit
31 Enhancement processing unit
100 Electronic scope
200 Processor
300 Monitor

The invention claimed is:

1. A processor for an electronic endoscope, which acquires a captured image of a living tissue and performs enhancement processing, comprising:
 a region detection unit configured to detect an enhancement processing target region to be enhanced from pixel information of the captured image of the living tissue; and
 an enhancement processing unit configured to perform enhancement processing on the enhancement processing target region detected by the region detection unit,
 wherein the region detection unit is configured to perform:
  a candidate extraction process of extracting a focused pixel as a candidate for an enhancement processing target region when a signal level value of the focused pixel is smaller than signal level values of two farthest pixels located on both sides farthest from the focused pixel in each of four pixel array directions of an up-down direction, a left-right direction, an upper left-lower right direction, and an upper right-lower left direction in a region surrounded by a frame surrounding a region with the focused pixel as a center, and
  a determination process of defining whether the number of times the focused pixel has been extracted as the candidate for the enhancement processing target region among the four pixel array directions in the candidate extraction process exceeds a preset threshold count, and
 wherein the region detection unit is configured to set the focused pixel as the enhancement processing target region when the number of times the focused pixel has been extracted as the candidate for the enhancement processing target region exceeds the preset threshold count, and repeat the candidate extraction process and the determination process while changing the frame size when the number of times the focused pixel has been extracted as the candidate for the enhancement processing target region does not exceeds the preset threshold count.

2. The processor for an electronic endoscope according to claim 1, wherein
 when a difference between each of the signal level values of the farthest pixels and the signal level value of the focused pixel is larger than a threshold 1, which is 2 or more at least at a discretized signal level in the signal level value, the region detection unit defines the focused pixel as the candidate for the enhancement processing target region.

3. The processor for an electronic endoscope according to claim 2, wherein the threshold 1 is larger as the size of the frame is larger.

4. The processor for an electronic endoscope according to claim 2, wherein
 the threshold 1 is set according to a location of an organ in a body cavity that is an object of the captured image.

5. The processor for an electronic endoscope according to claim 1, wherein
 the region detection unit is configured to determine whether the focused pixel is the candidate for the enhancement processing target region when an absolute value of a difference of each of the signal level values of the farthest pixels with respect to the focused pixel is smaller than a threshold 2.

6. The processor for an electronic endoscope according to claim 1, wherein
the frame is a frame of (2·i+1)×(2·i+1) pixels, where i is a natural number from 1 to 6.

7. The processor for an electronic endoscope according to claim 1, wherein
the enhancement processing is processing of reducing the signal level value of the detected enhancement processing target region.

8. The processor for an electronic endoscope according to claim 7, wherein
the signal level value is a signal level value of a luminance signal of the captured image, or a signal level value of an R component among RGB components of the captured image.

9. An electronic endoscope system comprising:

the processor for an electronic endoscope according to claim 1; and an electronic endoscope which is connected to the processor for an electronic endoscope and outputs the captured image of the living tissue.

* * * * *